(12) United States Patent
Kataoka (10) Patent No.: US 6,908,761 B1
(45) Date of Patent: Jun. 21, 2005

(54) TRANSCRIPTIONAL ACTIVATORS

(75) Inventor: Kohsuke Kataoka, Nerima-ku (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/129,192

(22) PCT Filed: Feb. 15, 2000

(86) PCT No.: PCT/JP00/00841

§ 371 (c)(1),
(2), (4) Date: May 2, 2002

(87) PCT Pub. No.: WO01/32860

PCT Pub. Date: May 10, 2001

(30) Foreign Application Priority Data

Nov. 4, 1999 (JP) .......................................... 11/314335

(51) Int. Cl.[7] .......................... C12N 1/00; C12N 15/00; C12N 15/09; C12N 15/63; C12N 15/70
(52) U.S. Cl. ..................... 435/320.1; 435/325; 424/617; 536/24.1
(58) Field of Search ....................... 424/617; 435/320.1, 435/325; 536/24.1

(56) References Cited

U.S. PATENT DOCUMENTS 4,201,775 A    5/1980   Filan et al.

FOREIGN PATENT DOCUMENTS

JP    8-301875    11/1996

OTHER PUBLICATIONS

Kataoka et al. Nukinzoku Ion Ni Yoru Mare Karen CiS–DNA Hairetsu No Tensha Kasseika, Dai 58kai,Nippon Gan Gakkai Soukai Kiji, Nippon Gan Gakkai, p. 483, column 1945 (1999), Applicant's IDS.*

Matsushima–Hibiya et al. Rat Maf–related factors: the specificities of DNA binding and heterodimer formation Biochemical and biophysical Research Communications vol. 245, p412–418 1998.*

Kobayashi et al, *J. of Biol. Chem.*, 274(10):6443–6452 (1999).

Kataoka et al, "Jukinzoku Ion Ni Yoru Mare Karen Cis–DNA Hairetsu No Tensha Kasseika", Dai 58kai, Nippon Gan Gakkai Soukai Kiji, Nippon Gan Gakkai, p. 483, column 1945 (1999).

* cited by examiner

*Primary Examiner*—James Ketter
*Assistant Examiner*—Konstantina Katcheves
(74) *Attorney, Agent, or Firm*—Sughrue Mion, PLLC (57) ABSTRACT

The invention provides a synthesis-inducible eucaryotic promoter having a transcriptional activity comprising, for example, a heavy metal-sensitive DNA sequence, derived from a natural promotor, of a base sequence of any one of SEQ ID NOS: 1 to 4; an inducer of the transcriptional activation activity thereof; a recombinant expression vector comprising a site for the insertion of an extraneous gene ligated to the above promotor: a eucaryotic expression kit comprising eucaryotic cells transfected with the above vector and the above inducer; and a method for expression of an extraneous gene in a eucaryotic system by using the same

12 Claims, 4 Drawing Sheets

SEQUENCE LISTING

```
<160> NUMBER OF SEQ ID NOS: 21

<210> SEQ ID NO 1
<211> LENGTH: 13
<212> TYPE: DNA
<213> ORGANISM: Artificial
<220> FEATURE:
<223> OTHER INFORMATION: Maf recognition element

<400> SEQUENCE: 1
tgctgactca gca                                                        13

<210> SEQ ID NO 2
<211> LENGTH: 13
<212> TYPE: DNA
<213> ORGANISM: Artificial
<220> FEATURE:
<223> OTHER INFORMATION: Maf recognition element

<400> SEQUENCE: 2
tgcttactaa gca                                                        13

<210> SEQ ID NO 3
<211> LENGTH: 13
<212> TYPE: DNA
<213> ORGANISM: Artificial
<220> FEATURE:
<223> OTHER INFORMATION: Maf recogntition element

<400> SEQUENCE: 3
tgatgactca tca                                                        13

<210> SEQ ID NO 4
<211> LENGTH: 13
<212> TYPE: DNA
<213> ORGANISM: Artificial
<220> FEATURE:
<223> OTHER INFORMATION: Maf recognition element
```

```
<400> SEQUENCE: 4
tgccgactca ttg                                                          13

<210> SEQ ID NO 5
<211> LENGTH: 13
<212> TYPE: DNA
<213> ORGANISM: Mouse
<220> FEATURE:
<221> NAME/KEY: misc_feature
<223> OTHER INFORMATION: Antioxidant responsive element of mouse

<400> SEQUENCE: 5
tggtgacaaa gca                                                          13

<210> SEQ ID NO 6
<211> LENGTH: 13
<212> TYPE: DNA
<213> ORGANISM: Artificial
<220> FEATURE:
<223> OTHER INFORMATION: Control sequence of Maf recognition element

<400> SEQUENCE: 6
tgaggactcc tca                                                          13

<210> SEQ ID NO 7
<211> LENGTH: 13
<212> TYPE: DNA
<213> ORGANISM: Artificial
<220> FEATURE:
<223> OTHER INFORMATION: AP-1 recognition element

<400> SEQUENCE: 7
ccatgactca ttg                                                          13

<210> SEQ ID NO 8
<211> LENGTH: 41
<212> TYPE: DNA
<213> ORGANISM: Rabbit
<220> FEATURE:
<221> NAME/KEY: misc_feature
<223> OTHER INFORMATION: Rabbit beta-globin TATA box

<400> SEQUENCE: 8
gatcttgggc ataaaaggca gagcactgca gctgctgctt a                           41

<210> SEQ ID NO 9
<211> LENGTH: 41
<212> TYPE: DNA
<213> ORGANISM: Rabbit
<220> FEATURE:
<221> NAME/KEY: misc_feature
<223> OTHER INFORMATION: Rabbit beta-globin TATA box

<400> SEQUENCE: 9
agcttaagca gcagctgcag tgctctgcct tttatgccca a                           41

<210> SEQ ID NO 10
<211> LENGTH: 13
<212> TYPE: DNA
<213> ORGANISM: Artificial
<220> FEATURE:
<223> OTHER INFORMATION: Linker sequence of MARE

<400> SEQUENCE: 10
tcgagctcgg aat                                                          13
```

```
<210> SEQ ID NO 11
<211> LENGTH: 6
<212> TYPE: DNA
<213> ORGANISM: Artificial
<220> FEATURE:
<223> OTHER INFORMATION: Linker sequence of MARE

<400> SEQUENCE: 11 ttactc                                                                6

<210> SEQ ID NO 12
<211> LENGTH: 9
<212> TYPE: DNA
<213> ORGANISM: Artificial
<220> FEATURE:
<223> OTHER INFORMATION: Linker sequence of MARE

<400> SEQUENCE: 12 cgagagtaa                                                             9

<210> SEQ ID NO 13
<211> LENGTH: 10
<212> TYPE: DNA
<213> ORGANISM: Artificial
<220> FEATURE:
<223> OTHER INFORMATION: Linker Sequence of MARE

<400> SEQUENCE: 13
attccgagct                                                           10

<210> SEQ ID NO 14
<211> LENGTH: 18
<212> TYPE: DNA
<213> ORGANISM: Artificial
<220> FEATURE:
<223> OTHER INFORMATION: Linker of pUC118

<400> SEQUENCE: 14
ggtaccactc gaggatcc                                                  18

<210> SEQ ID NO 15
<211> LENGTH: 18
<212> TYPE: DNA
<213> ORGANISM: Artificial
<220> FEATURE:
<223> OTHER INFORMATION: Linker sequence of pUC118

<400> SEQUENCE: 15
ggtaccactc gaggatcc                                                  18

<210> SEQ ID NO 16
<211> LENGTH: 13
<212> TYPE: DNA
<213> ORGANISM: Rat
<220> FEATURE:
<221> NAME/KEY: misc_feature
<223> OTHER INFORMATION: Antioxidant responsive element of rat GSt-Pi

<400> SEQUENCE: 16
ctatgattca gca                                                       13

<210> SEQ ID NO 17
<211> LENGTH: 13
<212> TYPE: DNA
<213> ORGANISM: Rat
```

-continued

```
<220> FEATURE:
<221> NAME/KEY: misc_feature
<223> OTHER INFORMATION: Antioxidant responsive element of rat GSt-Pi

<400> SEQUENCE: 17
cagtgacttg gca                                                    13

<210> SEQ ID NO 18
<211> LENGTH: 13
<212> TYPE: DNA
<213> ORGANISM: Rat
<220> FEATURE:
<221> NAME/KEY: misc_feature
<223> OTHER INFORMATION: Antioxidant responsive element of rat GSt-Pi

<400> SEQUENCE: 18
gggtgactca gca                                                    13

<210> SEQ ID NO 19
<211> LENGTH: 13
<212> TYPE: DNA
<213> ORGANISM: Rat
<220> FEATURE:
<221> NAME/KEY: misc_feature
<223> OTHER INFORMATION: Antioxidant responsive element of rat GSt-Pi

<400> SEQUENCE: 19
cgctgactca cgg                                                    13

<210> SEQ ID NO 20
<211> LENGTH: 32
<212> TYPE: DNA
<213> ORGANISM: Artificial
<220> FEATURE:
<223> OTHER INFORMATION: Oligonucleotide containing MARE sequence

<400> SEQUENCE: 20
tcgagctcgg aattgcttac taagcattac tc                               32

<210> SEQ ID NO 21
<211> LENGTH: 146
<212> TYPE: DNA
<213> ORGANISM: Artificial
<220> FEATURE:
<223> OTHER INFORMATION: 3xMARE/RBGP-Luc sequence

<400> SEQUENCE: 21
tcgagctcgg aattgcttac taagcattac tctcgagctc ggaattgctt actaagcatt   60
actctcgagc tcggaattgc ttactaagca ttactctcga ggatcttggg cataaaaggc  120
agagcactgc agctgctgct taagct                                      146
```

TRANSCRIPTIONAL ACTIVATORS

This is a National stage entry under 35 U.S.C. § 371 of application No. PCT/JP00/00841 filed Feb. 15, 2000; the disclosure of which is incorporated herein by reference.

TECHNICAL FIELD

The present invention relates to an improved synthesis-inducible eucaryotic promoter and an inducer which activates the transcriptional initiation of said promoter, particularly the inducer comprising a gold compound.

The present invention further relates to a recombinant expression vector having as ligated thereto said synthesis-inducible eucaryotic promoter, an expression kit comprising said recombinant expression vector and said inducer, and a novel method for expression of an extraneous gene which comprises using said kit.

BACKGROUND ART

As the mammalian expression promoter, the promoters present in the metallothionein (MT) gene and mouse mammary tumor virus-long terminal repeat (MMTV-LTR) have been broadly used. And as the inducer of the MT promoter, a heavy metal such as cadmium or zinc is generally considered to be the most appropriate.

The transcriptional activation by such a metal is mediated by a transcription factor bound to the inducible metal response element (MRE) present in the MT promoter. As response elements for transcriptional activation as occurring in promoters, it is known, as well as the above metal response elements, dexamethasone and other glucocorticoid response elements or hormone response elements, heat shock response elements, temperature response elements, interferon response elements, cytokine response elements, etc. Further known are expression systems each consisting of one or a combination of two or more of such response elements comprising specific sequences and a transcriptional activation inducer (e.g. Japanese Unexamined Patent Publication Nos. H07-501456, H07-83715 and H11-502705.).

Recently, MARE (Maf recognition element) has been discovered. The Maf tumor gene product discovered from chick retrovirus AS42 as a promoter activating the transcription of Maf is a transcription factor having a basic leucine zipper structure (bZip), which, as a homodimer, binds MARE (Maf recognition element) having a DNA sequence resembling TPA response element (TRE) and cAMP response element (CRE) to activate transcription (Igarashi, K., et al., Nature, 367, 568–572 (1994): Mol. Cell. Biol., 14, 700–712 (1994)).

For elucidating this transcription control mechanism mediated by MARE having said DNA sequence, the inventors investigated the responses of MARE to various stimuli at the cultured cell level. As a result, they discovered that the activity of said MARE becomes prominent in the presence of a compound of a heavy metal such as silver, mercury, cadmium or gold, for instance.

The object of the present invention is to provide a recombinant expression vector having an improved synthesis-inducible eucaryotic promter ligated thereto and a heavy metal compound serving as an inducer for activating the transcriptional initiation of this promoter and to thereby establish an expression system for an enhanced efficiency of expression of an extraneous gene.

After much investigation the inventors found that the above objects can be accomplished in accordance with the invention the principal features of which are now described hereunder and have developed the present invention.

DISCLOSURE OF INVENTION

The present invention provides a synthesis-inducible eucaryotic promoter having transcription activation activity comprising the following heavy metal-responsive DNA sequence (a) or (b) derived from the natural promoter: (a) the base sequence of any of SEQ ID NO: 1 through 4 (b) a base sequence homologous in at least 6 bases to the base sequence of SEQ ID NO: 1 and having transcription activation activity.

Particularly, the invention provides said synthesis-inducible eucaryotic promoter having a DNA sequence of any of SEQ ID NO: 1 through 4; said synthesis-inducible eucaryotic promoter which is responsive to a heavy metal selected from the group consisting of silver, mercury, cadmium and gold compounds; and said synthesis-inducible eucaryotic promoter wherein the metal compound is selected from the group consisting of (2,3,4,6-tetra-O-acetyl-1-thio-β-D-glucopyranosato-S) (triethylphosphine)gold, (1-thio-D-glucopyranosato)gold, and sodium aurothiomalate.

Furthermore, the invention provides an inducer for inducing the transcriptional activation activity of said synthesis-inducible eucaryotic promoter, which inducer is selected from the group consisting of heavy metal compounds, particularly said transcriptional activation inducer selected from the group consisting of silver, mercury, cadmium and gold compounds; and said transcriptional activation inducer which is a gold compound selected from the group consisting of (2,3,4,6-tetra-O-acetyl-1-thio-β-D-glucopyranosato-S)(triethylphosphine)gold, (1-thio-D-glucopyranosato)gold, and sodium aurothiomalate.

In addition, the invention provides a recombinant expression vector having a site for insertion of an extraneous gene linked to said synthesis-inducible eucaryptic promoter; a eucaryotic expression kit comprising eucaryotic cells transfected with said recombinant expression vector and said transcriptional activation inducer; and a method for expression of an extraneous gene in a eucaryotic system comprising bringing said recombinant expression vector harboring an extraneous gene into contact with said transcription activation inducer to activate the synthesis-inducible eucaryotic promoter in said vector to thereby promote induction of expression of the extraneous gene.

Particularly in the above method for expression, the transcriptional activation inducer is preferably one selected from the group consisting of compounds of silver, mercury, cadmium, and gold, more preferably one elected from among (2,3,4,6-tetra-O-acetyl-1-thio-β-D-glucopyranosato-S) (triethylphosphine)gold, (1-thio-D-glucopyranosato) gold, and sodium aurothiomalate.

By means of these synthesis-inducible eucaryotic promoter, transcriptional activation inducer, recombinant expression vector, and method for recombinant expression using them in accordance with the invention, the expression of an extraneous gene can be realized at a high rate as compared with the conventional extraneous gene expression technology. Also, the promoter of the invention can be utilized as a vector capable of inducing a drug for gene therapy.

Further, in accordance with the present invention, there can be developed an application technology which may comprise administering a gold compound to an experimental mouse and causing a disease-related gene to be induced in a knockout mouse or a transgenic mouse. Moreover, the kit of the present invention can be used as a kit for the induction of genes in cultured cells as well.

The following representation of amino acids, peptides, base sequences, and nucleic acids by abbreviations in this specification conforms to the rules of IUPAC-IUB [IUPAC-IUBC Communication on Biological Nomenchlature, Eur. J. Biochem., 138:9 (1984)], the Guideline for Drafting Patent Specifications and the Like which contain Nucleotide Sequences or Amino Acid Sequences (the Patent Office of Japan (ed.), and the conventions in the art.

Synthesis of DNAs, production of vectors (expression vectors) harboring an extraneous gene, host cells transfected with such vectors, and production of expressed proteins secreted by host cells, etc. can be easily carried out by the general genetic engineering techniques [Molecular Cloning, $2^{nd}$ Ed., Cold Spring Harbor Lab. Press (1989); Zoku Seikagaku Jikken Koza, "Idenshi Kenkyuho I, II, III" (Biochemical Experimental Series—Continued, "Methods for Gene Research I, II and III"), ed. by Japanese Biochemical Society (1986), etc.].

More particularly, DNAs can be synthesized by a chemical method of synthesis, such as the phosphoramidite method or the triester method, and can also be carried out by using a commercial automated oligonucleotide synthesizer. Double-stranded DNA fragments can be obtained from chemically synthesized single strands by a procedure comprising synthesizing complementary strands and annealing them under suitable conditions or coupling complementary strands by using a DNA polymerase together with suitable primer sequences.

The present invention is further concerned with a material and a method, which are effective in selective preparation of specific DNA sequences by external control of transcription.

Here, in one continuous DNA sequence, a certain DNA sequence situated forwardly of a given gene usually determines the site of initiation of transcription from DNA to mRNA. These are generally called promoter sequences. Other DNA sequences also bind proteins determinant of the frequency (or proportion) of transcription initiation upstream of a given gene in one continuous DNA sequence. These are known as regulator sequences. Thus, in one functional DNA sequence, the DNA sequences located forwardly of one selected gene and adapted to determine whether the transcription of the gene and subsequent expression of the gene take place is globally called a promoter sequence and a regulator sequence.

The promoter generally functions to modulate the transcription of a gene according to the physical and chemical conditions within and around a cell. And as a method for external modulation of the role of this promoter, that is to say the transcription of the gene sequence and expression thereof, one may discover an expression-inducing response element situated forwardly of one gene and specifying a responsive substance or factor to thereby insure a more positive insertion and stable integration of the DNA sequence into the cell.

The present invention provides a disclosure about the responsiveness of a specific promoter sequence to heavy metal, particularly a gold compound. As will be shown in the Examples presented hereinafter, the invention is based on the finding that a high rate of replication can be made possible by culturing a recombinant expression vector harboring an expressible extraneous gene linked to a promoter comprising a specific DNA sequence together with a heavy metal, particularly a gold compound, in eucaryotic cells.

The promoter of the present invention contains at least one natural inducible sequence. This may be an MARE sequence resembling AP1 sequence. Such an insert MARE may be a synthetic molecule comprising a pair of complementary oligonucleotides containing an MARE consensus sequence. A plurality of MAREs may be inserted into a natural promoter in the form of a linked sequence such as a double, triple or quadruple linkage or arbitrary base sequences may flank the MARE sequence in a linear sequence having a given length.

The promoter of the present invention may be a linked sequence containing a plurality of 13-nucleotide MARE sequences, such as those of SEQ ID NO: 1 to NO: 4, in a double, triple or quadruple fashion. In the present invention, the MARE sequence is defined with the DNA sequence of SEQ ID NO: 1 being taken as a standard. This includes a DNA sequence homologous in at least 6 nucleotides, preferably a DNA sequence homologous in at least 7 nucleotides, more preferably a DNA sequence homologous in at least 8 nucleotides, still more preferably a DNA sequence homologous in at least 9 nucleotides, most preferably a DNA sequence homologous in at least 10 nucleotides, which has a transcription activation function. Specific examples of such base sequence are shown in SEQ ID NO: 2–4 and SEQ ID NO: 16–19.

The particularly preferred embodiment of the invention includes a promoter having an insertion site enabling expression of an extraneous gene as modified to contain at least one inducible MARE, preferably entailing an enhanced gene product expression, so that, in a eucaryotic expression system, particularly a mammalian expression system, a gene expression is accomplished at induction of MARE.

This particularly preferred embodiment can be implemented by substitution-inserting a plurality of MARE sequences into the promoter region of a known replicatable vector and ligating them either directly or through a linker.

A specific example of such DNA sequence is shown in SEQ ID NO: 20 which is a DNA sequence provided with 3 units of the DNA sequence containing the MARE of SEQ ID NO: 2. More specific example of the DNA sequence is shown in SEQ ID NO: 21. Of course, the above MARE sequence is not restricted to SEQ ID NO: 2 but may for example be any of the other MARE sequences of SEQ ID NO: 1, 3 and 4 or any of the ARE sequences of SEQ ID NO: 16–19, and is not only restricted to repeats of the same MARE sequence or ARE sequence but may be a combination of different MARE sequences and/or different ARE sequences.

The sequence of SEQ ID NO: 5 and the sequences of SEQ ID NO: 16–19 are partial sequences of known mouse, rat, rat, mouse and human genes, respectively, and these known genes are described in the following literature.

Mouse GST-Ya: Biochemical and Biophysical Research Communication, 236, pp. 313–322 (1997)

Rat GSt-Pi: Proc. Natl. Acad. Sci., USA., 85, pp. 9456–9460 (1988)

Rat NADP: Quinone oxydoreductase: J. Biol. Cell, 268, pp. 19875–19881 (1993)

Mouse hemo oxygenase-1: Biochemical and Biophysical Research Communication, 221, pp. 570–576 (1996)

Human γ-glutamycysteine synthetase: J. Biol. Cell, 273, pp. 7445–7454 (1997)

Referring to the replicatable vector for use in the present invention, in cases where procaryotic cells are to be used as the host, a vector replicatable in the particular host cells is provided with a promoter, SD (Shine-Dalgarno) sequence, and an initiation codon (e.g. ATG) necessary for initiation of protein synthesis upstream of the particular gene so that the gene of the invention may be expressed in said vector and the resulting expression plasmid is used with advantage. As the vector mentioned above, generally plasmids derived from *Escherichia coli*, for example pBR322, pBR325, pUC12, pUC13, etc., are frequently used. However, these are not exclusive choices but various other known vectors can be utilized. Commercial vectors in the *E. coli* expression system include, for example, pGEX-4T (Amersham Pharmacia Biotech), pMAL-C2, pMA1-P2 (New England Biolabs), pET21, pET21/1acq (Invitrogen) and pBAD/His (Invitrogen).

For cases in which vertebrate cells are used as the host, the expression vector contains a promoter upstream of the gene of the invention which is to be expressed, RNA splicing sites, polyadenylation site, and transcription termination sequence. This vector may optionally have a replication origin. A specific example of such vector is pSV2 dhfr harboring the early promoter of SV40 [Mol. Cell. Biol., 1:854 (1981)].

Aside from the above, various known commercial vectors can be employed. Commercial vectors for use in expression systems utilizing animal cells include, for example, PEGFP-N, pEGFP-C (Clontech), pIND (Invitrogen) pcDNA3.1/His (Invitrogen) and like vectors for animal cells; and pFastBac HT (GibciBRL), pAcGHLT (PharMingen), pAc5/V5-His, pMT/V5-His, pMT/Bip/V5-his (all Invitrogen) and like vectors for insect cells.

A specific example of the expression vector which can be employed when yeast cells are used as the host is pAM82 having a promoter for the acid phosphatase gene [Proc. Natl. Acad, Sci., USA., 80:1 (1983)]. Commercial expression vectors for yeast cell use include PPICZ (Invitrogen), pPICZa (Invitrogen), etc.

The heavy metal-responsive DNA sequence derived from a natural promoter, more specifically a MARE sequence, can be substituted for any desired insertion site of a known promoter. The substituted promoter, that is the promoter having an MARE sequence inserted, can be used as the objective promoter having a heavy metal transcriptional activation activity.

More particularly, by removing at least one constitutive sequence of a promoter and/or inserting at least one MARE sequence in said constitutive sequence region, the particular promoter can be disabled. In the EXAMPLES section which appears hereinafter, there is presented a case in which such a constitutive sequence is disabled by applying both of the procedures, namely removal of said constitutive sequence and insertion of one or more MARE sequences.

Insertion of an MARE sequence may be insertion of a synthetic molecule consisting of a pair of complementary oligonucleotides containing a MARE consensus sequence. The objective promoter may also be obtained by inserting a plurality of MARE sequences in the form of a linked sequence.

The particularly preferred embodiment of the present invention includes a rabbit β-globin promoter of the SV40 origin as modified so as to contain at least one inducible MARE sequence so that in a eucaryotic expression system the gene expression effect may be accomplished at induction of the inducible MARE, preferably accompanied by an enhanced global level of gene expression. In this particularly preferred embodiment, a plurality of MARE sequences are inserted into the rabbit β-globin promoter derived from the natural SV40. A specific example of a plurality of MARE sequences is shown in SEQ ID NO: 21.

The promoter substitutable with MARE sequences is not particularly restricted, either, but when a strain of the genus *Escherichia* is used as the host, tryptophan (trp) promoter, lpp promoter, lac promoter, recA promoter, PL/PR promoter, etc. can be used with advantage. When the host is a strain of the genus *Bacillus*, SP01 promoter, SP02 promoter, penP promoter, etc. are preferred. As the promoter for use when the host is a yeast, pH05 promoter, PGK promoter, GAP promoter, ADH promoter, etc. can be used with advantage. The preferred promoter for cases where animal cells are used as the host includes SV40-derived promoter, retrovirus promoter, metallothionein promoter, heat shock promoter, cytomegalovirus promoter, and SRA promoter.

It should be understood that as the expression vector for the gene of the invention, the ordinary chimeric protein expression vector can also be used with advantage. A specific example of this vector is pGEX (Promega) for the expression of a chimeric protein with glutathione-S-transferase.

The novel synthesis-inducible eucaryotic promoter, particularly in cases where it is operatively linked to the gene to be expressed by an expression system, may be integrated into a vector for eucaryotic expression of the gene product. Such expression system includes eucaryotic cells transfected with the vector, particularly mammalian cells, for example Vera, CHO, HeLa, Rat II fibroblast cells and digestive tract epithelial cells transfected with the vector.

In connection with the above, substitution and insertion of the objective MARE sequence into the promoter can be easily carried out by the routine genetic engineering technology.

Thus can be constructed a recombinant expression vector having a site for insertion of an extraneous gene linked to the synthesis-inducible eucaryotic promoter containing a heavy metal response element and having transcriptional activation activity according to the invention.

The method of causing expression of the objective extraneous gene from the improved recombinant expression vector of the invention and producing a recombinant polypeptide as the expression product comprises constructing a recombinant DNA (expression vector) enabling an extraneous gene coding for the desired protein to be expressed in host cells, transfecting the host cells, growing the resulting transformant, and recovering the polypeptide from the culture obtained.

As the host cell, whichever of procaryotic and eucaryotic cells can be employed. Thus, the procaryotic host cell includes a broad spectrum of ordinary bacterial strains such as those of *Escherichia coli* and *bacillus subtilis*, preferably *Escherichia coli* strains, e.g. *E. coli* K12, in particular. The eucaryotic host cell includes vertebrate and yeast cells, the preferred examples of the former being the monkey cell line COS [Cell, 23: 175 (1981)], Chinese hamster ovarian cell line and its dihydrofolate reductase-deficient cell line [Proc. Natl. Acad. Sci., USA., 77:4216 (1980)], etc. As to the latter, *Saccharomyces* yeast cells, for instance, can be used with advantage. Of course, these are not exclusive choices.

The method for introduction of the desired recombinant DNA (expression vector) into host cells and the transformation method using the same are not particularly restricted but the various routine methods can be utilized.

The transformant obtained can be cultured in the routine manner and by this culture, the objective protein encoded by the designed extraneous gene is expressed and produced (accumulated or secreted) intracellularly, extracellularly or on the cell membrane of the transformant.

As the medium for use in carrying out this culture, various media which are in routine use for the adopted host cells can be selectively used and the cultivation can also be carried out under conditions favoring growth of the host cells.

The procedure for causing an extraneous gene coding for the desired protein to be expressed in host cells may comprise constructing a recombinant expression vector according to the invention in the first place, transfecting the host cells by introducing the vector, growing the resulting transformant cells, and stimulating the expression by adding a heavy meal having the property to induce the transcriptional activity of the synthesis-inducible eucaryotic promoter of the invention, whereby the objective protein can be produced with efficiency and on a high production scale.

Here, as the heavy metal (transcriptional activation inducer) which acts on the heavy metal response element, that is to say the MARE sequence, of the promoter of the invention, gold, cobalt, silver, mercury, cadmium, and compounds of these metals are exemplified. The preferred metals are gold, mercury, cadmium, and gold compounds. The inducer is not restricted to said heavy metal compounds but may be in any other form, such as a metal ion, that is capable of acting on the transformant to stimulate the expression.

The heavy metal compound as the above-mentioned inducer which influences the DNA sequence of the MARE (heavy metal response sequence) to evoke transcriptional activation and expression stimulation can usually be easily caused to form a pharmacologically acceptable salt with an ordinary acid and such a salt is also subsumed in the concept of the inducer of the invention as is the free compound. The acid which may form such a pharmacologocially acceptable salt includes inorganic acids such as hydrochloric acid, sulfuric acid, nitric acid, hydrobromic acid, etc. and organic acids such as acetic acid, p-toluenesulfonic acid, ethanesulfonic acid, oxalic acid, maleic acid, fumaric acid, citric acid, succinic acid, malic acid, benzoic acid, and so forth. Cobalt chloride, cadmium sulfide, mercury chloride, sodium tetrachloroaurate (III), and sodium aurothiomalate are specific examples of the inducer of the invention. In addition, metal adducts of saccharides or polysaccharides, such as glucopyranosato, S-glucopyranoside, S-glucose, S-maltose, S-fructose, N-glucopyranoside, N-glucose, N-maltose, N-fructose, P-glucopyranoside, P-glucose, P-maltose, P-fructose, etc. can also be exemplified as other inducer of the invention. More particularly, the inducer includes (2,3,4,6-tetra-O-acetyl-1-thio-$\beta$-D-glucopyranosato-S)(triethylphosphine)gold: auranofin, and (1-thio-D-glucopyranosato)gold. These heavy metal compounds, for example gold-containing compounds, can be produced by the conventional technology. For example, gold-containing compounds can be produced by the processes described in Japanese Unexamined Patent Publication Nos. S61-26916 and S53-132528.

The above metal compound can be utilized as a transcription activator in the method of expressing an extraneous gene according to the invention, such as gene therapy, by using the recombinant expression vector of the invention, and in such cases, it is generally used in the form of an ordinary pharmaceutical preparation. Such a preparation can be produced by using a diluent or excipient, such as the conventional filler, extender, binder, humectant, disintegrator, surfactant, lubricant, and so forth. The pharmaceutical preparation can be provided in various dosage forms selected according to the therapeutic objective and, as representative forms, includes tablets, pills, powders, solutions, suspensions, emulsions, granules, capsules, suppositories, injections (solutions, suspensions, etc.), eye-drops, nose-drops, and inhalants.

The amount of the active ingredient compound to be formulated in said transcription activator preparation is not particularly restricted but can be judiciously selected from a broad range. Usually, it may be 0.1–70 weight %, preferably 0.5–30 weight %, based on the total composition.

The method of administering said transcription activator is not particularly restricted but is selected according to the dosage form, the patient's age, sex and other factors, severity of illness, and other circumstances. Tablets, pills, solutions, suspensions, emulsions, granules and capsules are administered orally. Injections are administered either alone or in admixture with glucose, amino acid or other ordinary infusion by the intravenous route or, where necessary, administered alone by the intramuscular, intradermal, subcutaneous or intraperitoneal route. Suppositories are administered rectally. eye-drops are instilled into the eye and nose-drops into the nostrils, and inhalants are administered into the oral cavity.

The dosage of the transcription activator can be judiciously selected according to the administration method, the patient's age, sex and other factors, severity of illness, and other conditions, and usually the amount of the active ingredient heavy metal compound to be given daily to an adult patient can be selected from the range of about 0.1–30 mg per kg body weight. It is also recommendable to insure that the unit dosage form contains about 1–1000 mg of the active ingredient.

As mentioned above, administration of the transcriptional activation inducer (transcription activator) of the invention results in promotion of the operation of the objective synthesis-inducible eucaryotic promoter in the cultured cells or mammalian animal cells into which the transformant (expression vector) has been integrated so that the induction of expression of the recombinant expression vector can be encouraged. In this manner, the desired extraneous gene expression product can be produced with good efficiency on a high production scale.

The recombinant protein obtainable by the method for extraneous gene recombinant expression according to the invention can be optionally isolated and purified by various separatory procedures utilizing its physical, chemical and other properties [Biochemical Data Book II, pp. 1175–1259, First Edition, First Impression, June 23, 1980, published by Kabushiki Kaisha Tokyo Kagaku Dojin; Biochemistry, 25 (25), 8274 (1986); Eur. J. Biochem., 163, 313 (1987), etc.].

The relevant technology specifically includes the routine reconstitution treatment, treatment with a protein precipitating agent (salting-out), centrifugation, osmotic shock method, sonic disruption, ultrafiltration, molecular sieves chromatography (gel filtration), adsorption chromatography, ion exchange chromatography, affinity chromatography, high performance liquid chromatography (HPLC) and other liquid chromatography, dialysis and various combinations of said techniques. The particularly preferred technique is affinity chromatography utilizing a column to which an antibody specific to the objective extraneous protein has been coupled.

A working example of the above extraneous gene recombinant expression method according to the invention is a gene therapy. This gene therapy includes the gene therapy of a disease through the provision of a sense drug for creating mRNA and promoting translation to enhance the level of expression of an extraneous gene in the target cell by use of a recombinant expression vector capable of expressing the objective extraneous gene according to the invention.

According to the above gene therapy using a sense oligonucleotide, the desired medicinal effect can be achieved by integrating said sense oligonucleotide in the retrovirus, adenovirus, or AAV-derived recombinant expression vector of the invention, infecting pancreatic a cells with the construct, and administering the transcriptional activation inducer (heavy metal compound) of the invention to thereby enhance the efficiency of expression of said sense oligonucleotide.

The gene therapy vectors for introducing the desired gene for both recombination and extrachromosomal maintenance are already known in the art and any of such known vectors can be utilized in the present invention. For example, a virus vector or plasmid vector is used which contains an oligonucleotide copy of the desired extraneous gene as linked to the MARE (heavy metal response element) sequence and is capable of expressing the corresponding oligonucleotide product within the target cells. As such a vector, the expression vectors mentioned above can be used but the preferred are the vectors prepared by using the vectors disclosed in U.S. Pat. No. 5,252,479 and PCT WO93/07282 (pWP-7A, pWP-19, pWU-1, pWP-8A, pWP-21, pRSVL. etc.), pRC/CMV (Invitrogen), etc. as origin vectors. The more preferred are the various virus vectors to be described hereinafter.

Introduction of the recombinant expression vector of the invention into cells can be carried out by the various methods known in the art for the introduction of DNA into cells, such as electroporation, calcium phosphate transfection or coprecipitation, viral transduction, and so forth. The cells transformed with the object oligonucleotide can be used in the per se isolated state as a drug for improving the human disease state associated with an extraneous gene or as a model system for therapeutic research.

In the gene therapy utilizing the present invention, the technology for introducing the desired gene into the target cells or tissue includes two representative methods.

The first method is one (an ex vivo technique) which comprises harvesting target cells from a patient to be treated, growing the cells ex vivo in the presence of a transcription activator comprising the transcriptional activation inducer of the invention as an active ingredient to introduce the oligonucleotide of the objective gene harbored by a retrovirus vector, and retransplanting the resulting cells. This method is suitable for the therapy of genetic diseases associated with defective genes, such as ADA deficiency, cancers and AIDS.

The second method is a gene direct introduction method (direct technique) which comprises injecting the objective oligonucleotide (the oligonucleotide of the objective extraneous gene) directly into the patient's body or target site such as a tumor tissue.

More particularly, said first method for gene therapy is carried into practice, for example as follows. Thus, the method comprises separating the mononuclear cells harvested from a patient (from monocytes) with a blood fractionator, growing the separated cells in the presence of a transcription activator comprising the inducer of the invention as an active ingredient in a suitable medium such as AIM-V medium for about 72 hours, and adding the recombinant expression vector of the invention which contains the oligonucleotide to be introduced (the oligonucleotide of the objective gene). In order to enhance the introduction efficiency of the oligonucleotide, the cells are optionally centrifuged at 2500 rpm in the presence of protamine at 32° C. for 1 hour and, then, cultured in 10% carbon dioxide atmosphere at 37° C. for 24 hours. After the above procedure is repeated several times, the cells are further cultured in the presence of the transcription activator comprising the inducer of the invention as an active ingredient in a medium, such as AIM-V medium, for 48 hours and, then, washed with saline. The viable cell count is recorded and the efficiency of introduction of the sense oligonucleotide is determined by in situ PCR or, when the object of interest is enzymatic activity, the degree of activity is measured to confirm the effect of introduction of the objective oligonucleotide.

Then, safety checks, such as culture for bacteria and fungi among cultured cells, test for mycoplasma infection, and search for endotoxins, are made and, after confirmation of safety, the cultured cells transfected with the predicted effective dose of the sense oligonucleotide (the oligonucleotide of the objective gene) are returned to the patient by intravenous drip. The gene therapy is consummated as the above procedure is repeated at an interval of, for example, a few weeks through a few months.

The dosage of the virus vector is judiciously selected according to the target cells. Usually, the preferred dosage in terms of virus titer may for example be in the range of $1 \times 10^3$ cfu to $1 \times 10^8$ cfu for $1 \times 10^8$ target cells.

An alternative embodiment of the above first method comprises co-growing viral cells transfected with a retrovirus vector containing the objective sense oligonucleotide (the oligonucleotide of the objective gene) together with the patient's cells to introduce the oligonucleotide (the oligonucleotide of the objective gene) into the target cells.

In conducting the second method (direct technique) for gene therapy, it is good practice to carry out an ex vivo preliminary experiment in advance, by a PCR search for the vector gene cDNA or an in situ PCR analysis, to see whether the objective oligonucleotide (the oligonucleotide of the objective gene) may be actually introduced by this gene introduction method or whether an elevation of specific activity or growth or growth inhibition of target cells, which is the expected therapeutic effect of introduction of the objective sense oligonucleotide (the oligonucleotide of the objective gene), may actually take place. Furthermore, when a virus vector is employed, it is of course important to confirm the safety of oligonucleotide introduction for gene therapy by carrying out a PCR search for proliferative retrovirus, measuring reverse transcriptase activity, or performing a PCR monitor of the membrane protein (env) gene.

The present invention further provides a pharmaceutical composition or pharmaceutical preparation (gene therapeutic agent) comprising cells transfected with the recombinant expression vector or the objective oligonucleotide (the oligonucleotide of the objective gene) of the invention as an active ingredient in a pharmaceutically effective amount and a suitable nontoxic pharmaceutical carrier or diluent.

The pharmaceutical carrier which can be formulated in the pharmaceutical composition (pharmaceutical preparation) of the present invention includes those diluents, excipients and the like which are generally used according to dosage forms, such as fillers, extenders, binders, humectants, disintegrators, surfactants, lubricants, and so forth. These can be selectively used according to the unit dosage form for the preparation.

The unit dosage forms for the pharmaceutical preparation of the invention may be the same as those mentioned for the preparation of the polypeptide encoded by the objective gene, and can be judiciously selected from various forms according to therapeutic purposes.

For example, the pharmaceutical preparation containing the recombinant expression vector of the invention is prepared in the form in which the vector is entrapped in liposomes or in the form of cultured cells infected with a virus containing a retrovirus vector harboring the desired sense oligonucleotide. These may further be processed into such forms as formulated in phosphate-buffered saline (pH 7.4), in Ringer's solution, or in an injectable intracellular composition fluid. Furthermore, they may be provided in such forms as can be administered together with a substance conducive to an increased gene introduction efficiency, such as protamine.

The method for administration of said pharmaceutical preparation is not particularly restricted but can be selected according to the dosage form, the patient's age, sex and other factors, and severity of illness, among other conditions. The amount of the active ingredient to be contained in said pharmaceutical preparation and the dosage thereof are not particularly restricted but can be liberally selected from a broad range in consideration of the expected therapeutic efficacy, the method of administration, the period of treatment and the patient's age, sex, and other factors, among others.

Generally, the dosage of the objective sense oligonucleotide-containing retrovirus vector as a pharmaceutical preparation per kg body weight for an adult human may for example be selected, as rule of the thumb, from the range of about $1 \times 10^3$ pfu through about $1 \times 10^{15}$ pfu in terms of retrovirus titer.

In the case of cells caused to contain the objective oligonucleotide or the recombinant expression vector of the invention, the proper dosage may be selected from the range of about $1 \times 10^4$ cells/body through $1 \times 10^{15}$ cells/body.

This pharmaceutical preparation can be administered once daily or in a few divided doses a day, or administered intermittently at an interval of 1 to a few weeks. Preferably, the transcriptional activation inducer of the invention (transcription activator) can be administered in combination with a substance capable of increasing the efficiency of gene introduction, such as protamine, or a pharmaceutical preparation containing the same.

The method for extraneous gene expression according to the present invention can be applied to drug screening and, as such, the present invention further provides a method for drug screening. This screening method can be carried out by using an extraneous gene expression system comprising a nonfunctional extraneous gene according to the invention or cells expressing an extraneous gene. By causing said extraneous gene expression system of the invention or cells expressing the extraneous gene to grow and multiply in the presence of a drug substance to be screened for a predetermined period of time and measuring the growth rate of the cells, it can be determined whether, for example, the candidate compound is capable of modulating the growth of cells, modulating protein-protein coupling, or modulating complex-forming ability. As a means for measuring the rate of growth or proliferation, the biological activity of the receptor of the extraneous gene may also be measured.

Furthermore, in accordance with the present invention, by constructing a knockout mouse (mutant mouse) harboring the target gene, it can be confirmed which site of the target gene sequence influences said changes in the cells or tissue in vivo, that is to say what functions the target extraneous gene product and the modified extraneous gene product discharge in vivo.

This method is a technique for intentional modification of the genetic information of a living organism by taking advantage of the homologous recombination of genes and includes the method using mouse embryonic stem cells (ES cells) as an example (Capecchi, M. R., Science, 244, 1288–1292 (1989)).

The above method of constructing a mutant mouse is a routine technology for those skilled in the art, and by applying a wild type gene of the object gene and a mutant gene, for instance, to this modifying technology (Jikken Igaku (Experimental Medicine), ed. by Tetsuo Noda, Supplement, 14 (20) (1996), Youdosha), a mutant mouse can be easily constructed. Therefore, through application of the above technology, it is possible to design and develop drugs having an improved biological activity of a given kind or stability or drugs acting as inhibitors, agonists or antagonists of a given biological activity.

Furthermore, the present invention provides a eucaryotic expression system or expression kit comprising eucaryotic cells transfected wtih a recombinant expression vector having a site for insertion of an extraneous gene for accomplishing an induced gene expression and a transcriptional activation inducer of the invention.

By utilizing the eucaryotic expression system or expression kit of the invention, detection of the objective extraneous gene, diagnosis of diseases related to the object gene, morbidity or status research, and studies on substances influencing the object gene, and influences of agonists and antagonists can be carried out so that great contributions may be made in the field of medicines and diagnoses.

BEST MODE FOR CARRYING OUT THE INVENTION

The following examples illustrate the present invention in further detail without defining the scope of the invention.

EXAMPLE 1

The following is an example showing the construction of an expression vector provided with a DNA sequence responsive to a heavy metal, particularly gold, that is to say the MARE sequence, in accordance with the invention and the effect of the invention through measurement of the activity of the expression vector.

(a) Construction of a Recombinant Vector

As the basal skeleton of the recombinant vector, pGL2-Basic (product of Promega) was used. This vector is a luciferse expression vector.

The SV40 promoter of the above pGL2-Basic was substituted with oligonucleotides (SEQ ID NO: 8 and NO: 9, 41-mer each) containing the TATA sequence of rabbit β-globin promoter at Bgl II/Hind III site to construct pRBGP3 (Nature, 367, 568–572 (1994)).

Then, 3 copies (Mol. Cell. Biol., 14, 700–712 (1994)) of various oligonucleotides (32-mers) containing the MARE sequences of SEQ ID NO: 1 through 7, comparative or control MARE sequences (SEQ ID NO: 1–4, 6 and 7), and an ARE sequence (SEQ ID NO: 5) were respectively inserted into the XhoI site of pUC118 vector with a modified poly-linker sequence. Further, the portion containing the 3 repeats of MARE sequence was excised at KpnI/BamHI site and inserted into the KpnI/BamHI site of pRBGP3. As an example of the above 32mer sequence, the one containing MARE of SEQ ID NO: 2 is shown in SEQ ID NO: 20. Here, tcgag represents the XhoI site.

Thus obtained were 3xMARE/RBGP-Luc and 3xARE/RBGP-Luc plasmids containing 3 repeats of 32 oligonucleotide sequences containing the 13 oligonucleotides shown in SEQ ID NO: 1 through 7 (MARE sequences, ARE sequences, and the corresponding comparative and control sequences). SEQ ID NO: 21 is an example of the sequence contained in the resulting 3xMARE/RBGP-Luc using SEQ ID NO: 2 as MARE. The obtained recombinant expression vectors were used for subsequent transfections.

(b) Method of expression

Transfections were carried out using SUPERFECT Transfection Reagent (Qiagen) according to the protocol accompanying the reagent. Human hepatocellular calcinoma cell line HepG2 was subcultured on a 35 mm plate and, after 24 hours, the transfection was carried out. Thus, a transfection solution containing 100 μl of a vector solution containing 0.25 μg of the above plasmid, 100 μl of SUPERFECT transfection reagent, and 600 μl of DMEM serum-free medium were added to a PBS-washed cell plate. After 2 hours of incubation at 37° C., the medium was changed to 10% FCS-supplemented DMEM. After 2 hours, stimulating reagents containing various heavy metal compounds inclusive of auranofin; Ridaura™, product of Sigma; 2,3,4,6-tetra-O-acetyl-1-thio-β-D-glucopyranosato-S)(triethylphosphine)gold were added and the culture was continued. The luciferase activity in the cells was assayed 15–18 hours later.

(c) Method of Activity Measurement

The assay of luciferase activity was carried out using Dual-Luciferase Reporter Assay System (product of Promega) according to the manufacture's protocol.

To the culture plate was added 100 μl of the cytolytic buffer included in the 200 μl kit to lyse the cells, and using a bench-top centrifuge, the lysate was centrifuged at 15,000 rpm for 5 seconds. The supernatant, 20 μl, of the lysate was mixed with 100 μl of the attached reagent LARII and the first chemiluminescence was measured with a luminometer. Then, 100 μl of the stopper (Stop & Glo Reagent) was added and the second chemniluminescence was measured.

The ratio of the first and second chemiluminescences was determined to calculate luciferase activity.

(1) Studies on the Effects of Various Heavy Metal Ions on the Meal Responsiveness of MARE Sequence The recombinant expression vector (reporter plasmid) ligated with the MARE sequence of SEQ ID NO: 2 as constructed under (a) above, namely 3xMARE/RBGP-Luc, was used. Stimulating reagents containing various heavy metal compounds, namely 100 μM each of manganese chloride ($MnCl_2$), cobalt chloride ($CoCl_2$), nickel chloride ($NiCl_2$), copper sulfate ($CuSO_4$), zinc sulfate ($ZnSO_4$), cadmium sulfate ($CdSO_4$), mercury chloride ($HgCl_2$) and sodium tetrachloroaurate(III) ($Na(AuCl_4)$) and 5 μM of auranofin, were respectively added and the cells were cultured by the above procedure (b) for 18 hours. Then, luciferase activity was measured by the procedure described under (c) above. The results are shown in FIG. 1.

Figure 1:
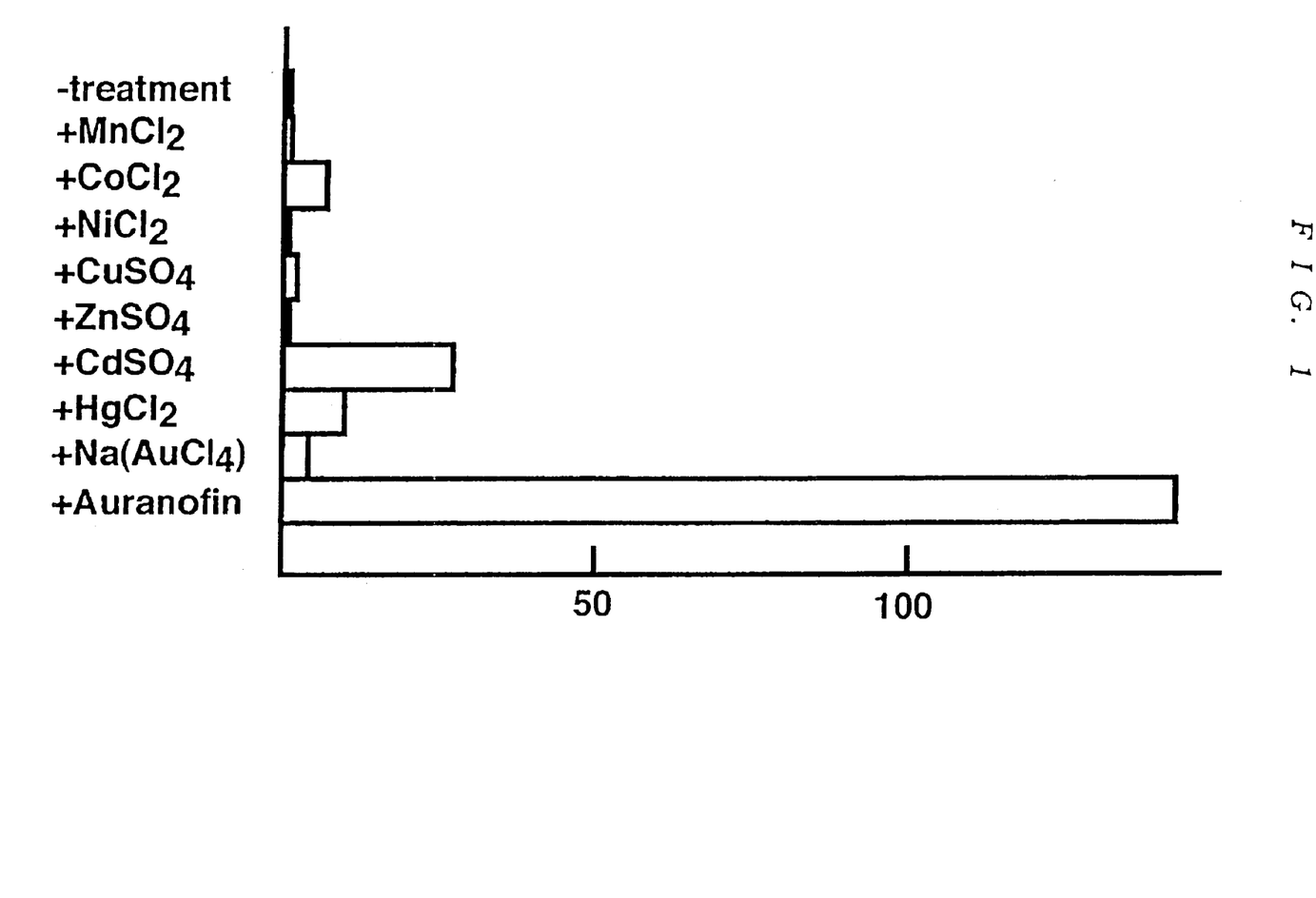
FIG. 1 is a graph showing the degree of activation of MARE resulting from addition of a metal compound which influences the transcription activity of the synthesis-inducible eucaryotic promoter of the invention.

In FIG. 1, "-treatment" represents a control without addition of any heavy metal compound and the abscissa (Fold Activation) represents the luciferase activity ratio with said control being taken as 1.

It was confirmed from FIG. 1 that, of the various heavy metals added, the luciferase activities in multiples of untreated control were 6.9 for cobalt chloride, 27.3 for cadmium sulfate, 10 for mercury chloride, and 4.3 for sodium tetrachloroaurate(III). Particularly with auranofin, the luciferase activity was prominently as high as 142.4 times.

(2) Studies on the Operation and Effect of Various Gold Compounds on MARE Sequence The recombinant expression vector (reporter plasmid) ligated with the MARE sequence of SEQ ID NO: 2 as constructed under (a) above, that is 3xMARE/RBGP-Luc, was used. According to the above method (b), 3 kinds of gold compounds were added: auranofin (represented by "AUR" on the drawing) at levels of 0.5, 1, 2, 5, 10 and 20 μM, (1-thio-D-glucopyranosato) gold ("AuTG" on the drawing) at levels of 20, 100, 250 and 500 μM, and sodium aurothiomalate ("AuTM" on the drawing) at levels of 10, 25, 50, 100, 250 and 500 μM, and the same test as (1) above was carried out. The results are shown in FIG. 2 (ordinate: luciferase activity ratio (Fold Activation), abscissa: the concentration of each compound).

Figure 2:
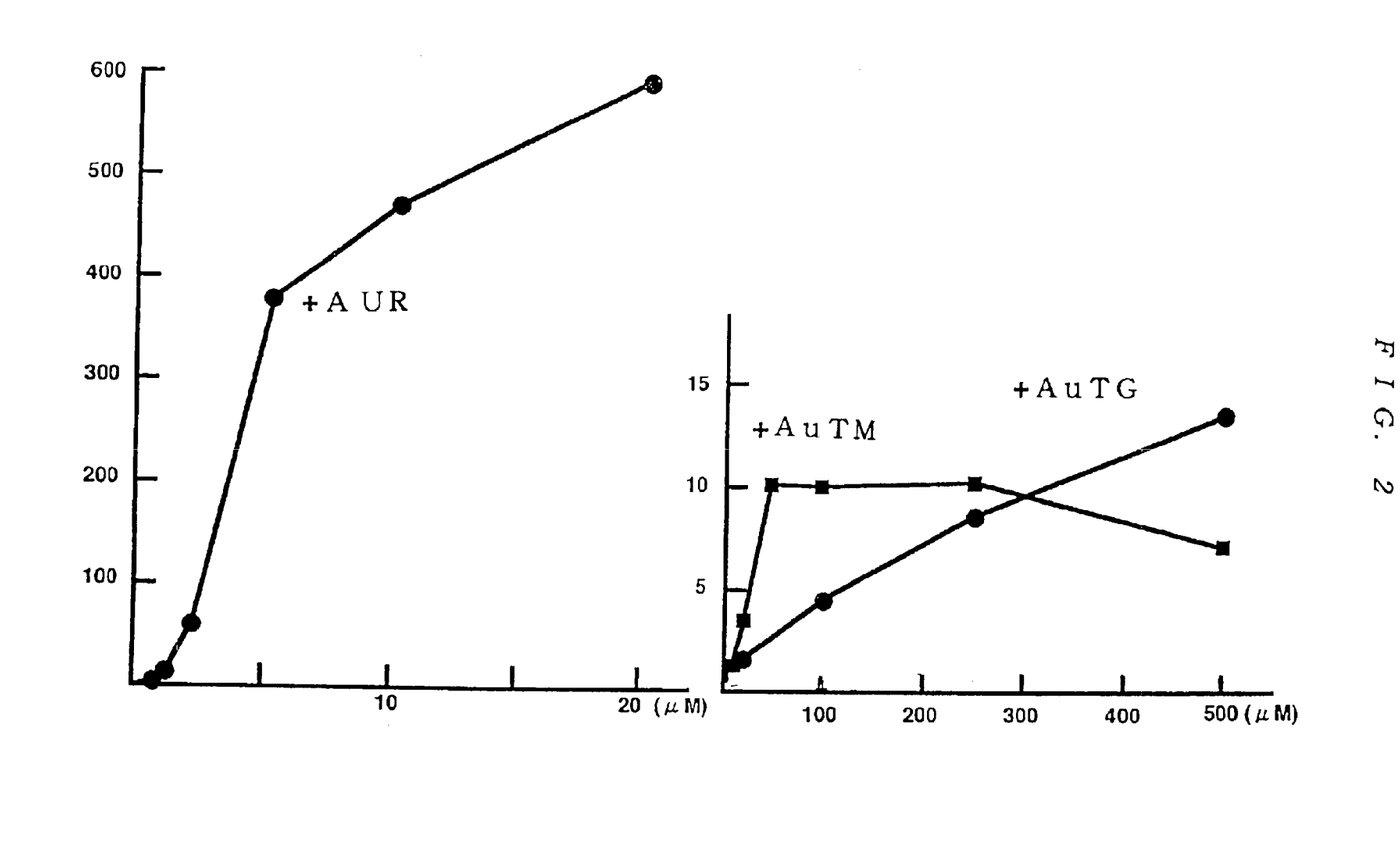
FIG. 2 is a graph showing the dose dependence of the degree of activation of MARE resulting from addition of the transcriptional activation inducer (gold compound) of the invention.

It was confirmed from FIG. 2 that the three kinds of gold compounds added activated MARE dose-dependently. Auranofin, in particular, caused outstanding luciferase activation compared with the other two kinds of gold compounds.

(3) Studies on the Operation and Effect of Auranofin on each MARE Sequence

The recombinant expression vectors (reporter plasmids) having as linked thereto the MARE sequences of SEQ ID NO: 1, 2, 3, 4, 6 and 7, respectively, namely 3xMARE/RBGP-Luc plasmids, and as positive controls, serum response element (SRE), namely 5xSRE (c-fos) [Cell, 42, pp. 889–902 (1985), SRE contained in c-fos promoter] and 5xkB (IL2R-a) [Oncogene, 10, pp. 1199–1207 (1995), the kB element contained in the IL-2 receptor-αpromoter], respectively, were constructed by the same procedure as described under (a).

It is known that SRE (serum response element) is activated by SRF (serum response factor), while kB is activated by NFkB (nuclear factor kB).

Each of the above vectors was cultured by the above procedure (b) for 18 hours in the presence of 5 μM auranofin or in the absence thereof and the luciferase activity was measured by the above procedure (c). The results are shown in FIG. 3 (ordinate: each vector, abscissa: luciferase activity ratio, top row; without auranofin, bottom row; 5 μM auranofin added).

Figure 3:
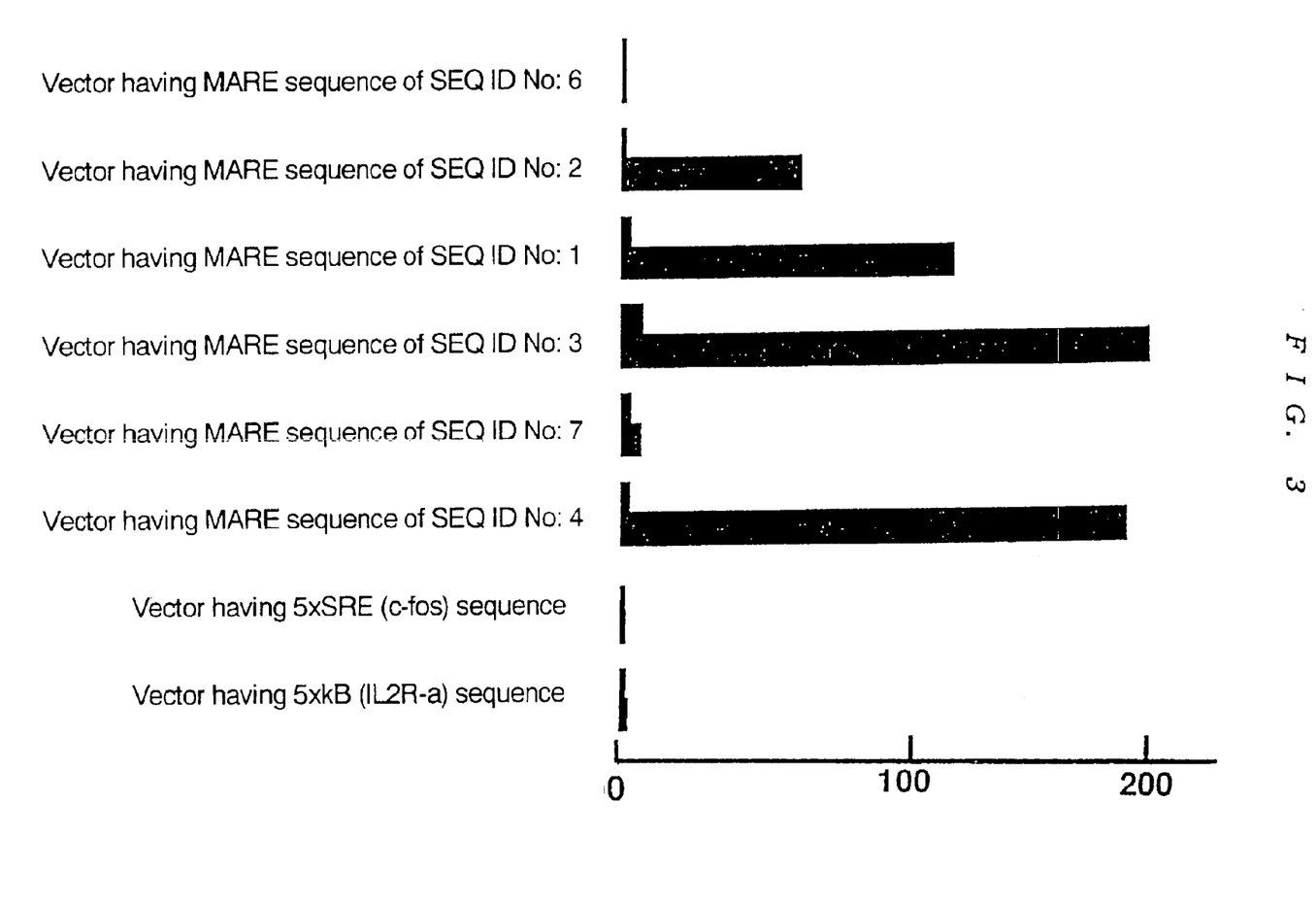
FIG. 3 is a graph showing the operation and effect of the transcriptional activation inducer (gold compound) of the invention on each MARE sequence.

It can be seen from FIG. 3 that auranofin does not act on any of the control MARE of SEQ ID No: 6, the AP-1 (activator protein-1) element of SEQ ID NO: 7, and the positive control sequences, namely 5xSRE (c-fos) and 5xkB (IL2R-a), but acts specifically on the respective MARE sequences of SEQ ID NO: 1, 2, 3 and 4. The transcription activity ratios on these MARE sequences were 53.3, 158.7, 30.8, and 112.9.

(4) Studies on the Operations and Effects of Various Gold Compounds on ARE Sequence The recombinant expression vector (reporter plasmid) having as linked thereto the ARE sequence of SEQ ID NO: 5, which resembles MARE in sequence, as constructed by the procedure described under (a), namely 3xARE/RBGP-Luc, was cultured by the above procedure (b) in the presence of 3 gold compounds, namely auranofin (AUR, 5μM), (1-thio-D-glucopyranosato)gold (AuTG, 500 μM) and sodium aurothiomalate (AuTM, 100 μM), respectively, or in the presence of thiomalate (TM, 100 μM), which is structurally related to sodium aurothiomalate but does not contain gold, or tBHQ (2,5-di-tert-butylhydroquinone, product of Wako, 60 μM), which is known to be an ARE transcription activator, as in (1) and the luciferase activity ratio was determined. The results are shown in FIG. 4 similar to FIG. 1 (the abbreviations of reagents added are the same as above;

each luciferase activity ratio was calculated with the control value found by culture of the vector in the absence of the test reagent being taken as 1).

Figure 4:
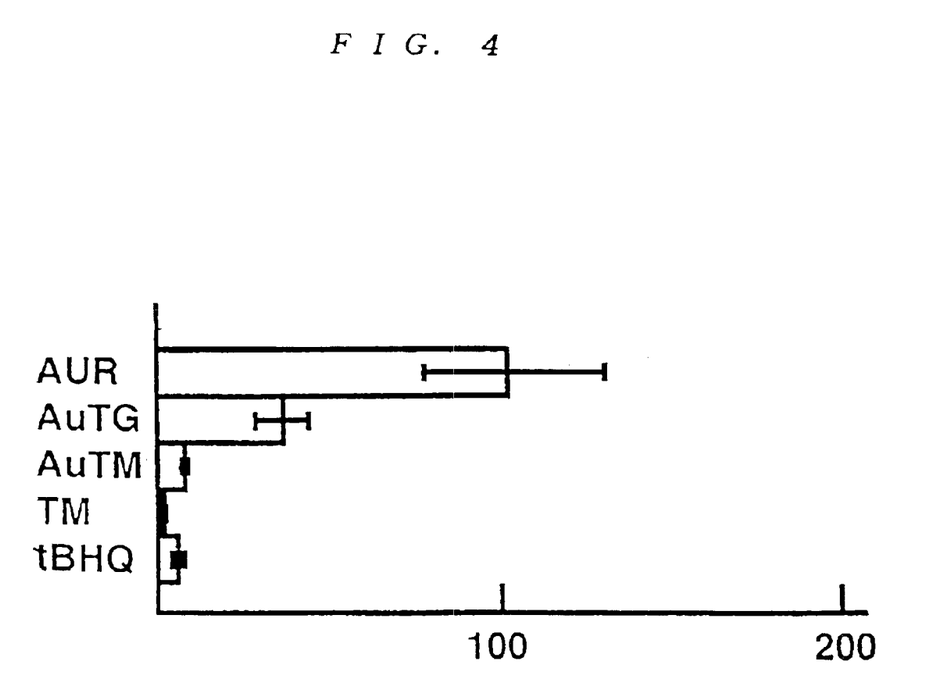
FIG. 4 is a graph showing the operation and effect of the transcriptional activation inducer (gold compound) on the ARE sequence.

It can be seen from FIG. 4 that on the reporter plasmid having as linked thereto the ARE sequence of the glutathione S-transferase Ya gene, each of auranofin, (1-thio-D-glucopyranosato)gold and sodium aurothiomalate acts as a transcriptional activation inducer. The degree of activation was either equivalent (AuTM; activity ratio: 8.1±0.4) to that of tBHQ (activity ratio: 6.0±3.8) or greater (AuTG; activity ratio: 21.7±15.4, AUR; activity ratio: 102.9±53.4). In the case of AUR, in particular, the activity was prominently as high as about 30 times that of tBHQ. In contrast, thiomalate which is structurally related to sodium aurothiomalate but lacks gold did not induce the transcriptional activation of ARE (activity ratio: 2.1±0.6).

It is apparent from the above test results that the MARE sequences and ARE sequences of SEQ ID NO: 1–5 and 7, that is to say the base sequences of SEQ ID NO: 1 and DNA sequences homologous thereto in at least 6 bases are heavy metal-responsive DNA sequences and, as such, cause the transcriptional activation of MARE and ARE in the presence of the particular heavy metal.

Furthermore, it was confirmed that on these MARE and ARE sequences, silver, cadmium, cobalt and gold, particularly gold compounds, are prominent in the effect of inducing the transcriptional activation of MARE and ARE.

Therefore, the expression system or expression kit comprising a recombinant expression vector to which any of the MARE sequence of SEQ ID NO: 1 and the sequences homologous thereto in at least 6 nucleotides has been bound or ligated and such a heavy metal compound can be utilized as a vector capable of inducing a drug for gene therapy or in application technologies where an experimental mouse is caused to ingest a heavy metal, particularly a gold compound, and thereby induce a disease-related gene in a knockout mouse or a transgenic mouse.

INDUSTRIAL APPLICABILTY

In accordance with the present invention there can be provided a vector capable of inducing a drug for gene therapy. Moreover, in accordance with the invention there can be provided an application technology wherein a disease-related gene can be induced in a knockout mouse or a transgenic mouse, for instance. Furthermore, in accordance with the present invention there can be provided a kit for induction of genes in cultured cells, for instance.

What is claimed is:

1. A kit comprising:
   (A) a eukaryotic cell harboring a recombinant vector having a site for insertion of exogenous DNA, wherein said site is operably linked to an inducible eukaryotic promoter, said eukaryotic promoter comprising the nucleotide sequence of SEQ ID NO: 2, and
   (B) a transcriptional activation inducer comprising a metal compound selected from the group consisting of a silver compound, a mercury compound, a cadmium compound, and a gold compound as an active ingredient.

2. The kit of claim 1, wherein said transcriptional activation inducer comprises a gold compound selected from the group consisting of (2,3,4,6 tetra-O-acetyl-1-thio-β-D-glucopyranosato-S)(triethylphosphine)gold, (1-thio-D-glucopyranosato)gold, and sodium aurothiomalate.

3. A method for inducing transcriptional activation of exogenous DNA comprising:
   providing a eukaryotic cell harboring a recombinant vector containing exogenous DNA operably linked to an inducible eukaryotic promoter, said eukaryotic promoter comprising the nucleotide sequence of SEQ ID NO: 2,
   contacting said eukaryotic cell with a transcriptional activation inducer, said inducer comprising a metal compound selected from the group consisting of a silver compound, a mercury compound, a cadmium compound and a gold compound as an active ingredient.

4. The method of claim 3, wherein said transcriptional activation inducer comprises a gold compound selected from the group consisting of (2,3,4,6 tetra-O-acetyl-1-thio-β-D-glucopyranosato-S)(triethylphosphine)gold, (1-thio-D-glucopyranosato)gold, and sodium aurothiomalate.

5. The kit of claim 1, wherein said eukaryotic cell is a mammalian cell.

6. The kit of claim 5, wherein said eukaryotic cell is selected from the group consisting of a Vera cell, a CHO cell, a HeLa cell, a Rat II fibroblast cell, and a digestive tract epithelial cell.

7. The kit of claim 2, wherein said eukaryotic cell is a mammalian cell.

8. The kit of claim 7, wherein said eukaryotic cell is selected from the group consisting of a Vera cell, a CHO cell, a HeLa cell, a Rat II fibroblast cell, and a digestive tract epithelial cell.

9. The method of claim 3, wherein said eukaryotic cell is a mammalian cell.

10. The method of claim 9, wherein said eukaryotic cell is selected from the group consisting of a Vera cell, a CHO cell, a HeLa cell, a Rat II fibroblast cell, and a digestive tract epithelial cell.

11. The method of claim 4, wherein said eukaryotic cell is a mammalian cell.

12. The method of claim 11, wherein said eukaryotic cell is selected from the group consisting of a Vera cell, a CHO cell, a HeLa cell, a Rat II fibroblast cell, and a digestive tract epithelial cell.

* * * * *